(12) United States Patent
Dong et al.

(10) Patent No.: US 6,331,565 B1
(45) Date of Patent: Dec. 18, 2001

(54) DICAFFEOYLQUINIC ACID FOR TREATING HEPATITIS B AND THE DISEASES ASSOCIATED WITH RETROVIRUS, AND THE NEW CAFFEOYLQUINIC ACID DERIVATIVES

(75) Inventors: Junxing Dong; Zhongming Tang; Zhibao Mi; Bingji Wang, all of Beijing (CN)

(73) Assignee: Institute of Radiation Medicine Academy of Military Medical Sciences of the PLA, Beijing (CN)

( * ) Notice: Subject to any disclaimer, the term of this patent is extended or adjusted under 35 U.S.C. 154(b) by 0 days.

(21) Appl. No.: 09/260,740

(22) Filed: Mar. 1, 1999

Related U.S. Application Data

(63) Continuation-in-part of application No. PCT/CN97/00087, filed on Aug. 27, 1997.

(30) Foreign Application Priority Data

Aug. 29, 1996 (CN) .................................................. 96111691

(51) Int. Cl.$^7$ ....................................................... A01N 37/10
(52) U.S. Cl. .............................. 514/532; 514/533; 560/75
(58) Field of Search ................................ 560/75; 514/532, 514/533

(56) References Cited

U.S. PATENT DOCUMENTS 5,445,816   8/1995   Li et al. ................... 424/62

FOREIGN PATENT DOCUMENTS

1472086 * 4/1977 (GB).

OTHER PUBLICATIONS

Current Structured Drugs, Wang Zemin, pp. 1529–1530, No. 4854, Jul., 1993.

* cited by examiner

Primary Examiner—Paul J. Killos
(74) Attorney, Agent, or Firm—Ladas & Parry

(57) ABSTRACT

This invention relates to the new use of dicaffeoylquinic acid derivatives for treating Hepatitis B and diseases associated with retrovirus (such as HIV), the new caffeoylquinic acid derivatives and the composition containing the same.

6 Claims, 3 Drawing Sheets

3.7Kb 0  15.625  31.25  62.5  125  250

DICAFFEOYLQUINIC ACID FOR TREATING HEPATITIS B AND THE DISEASES ASSOCIATED WITH RETROVIRUS, AND THE NEW CAFFEOYLQUINIC ACID DERIVATIVES

This application is a continuation-in-part of PCT/CN97/00087 (U.S. designation) filed Aug. 27, 1997.

FIELD OF THE INVENTION

The invention relates to the new use of dicaffeoylquinic acid derivatives for treating Hepatitis B and diseases associated with retrovirus (such as HIV), the new caffeoylquinic acid derivatives and the pharmaceutical composition containing the same.

PRIOR ART

Hepatitis B is a serious worldwide disease infected by hepatitis B virus. Over 300 million individuals are chronically infected with HBV. China is a highly epidemic area of hepatitis B. In addition to causing both acute and chronic liver diseases, HBV infection is epidemically associated with a high risk of developing cirrhosis and primary hepatocellular carcinoma in human. Several types of treatment regiments have been reported for individuals with chronic HBV infection, including interferons and nucleoside analogs. However, these treatments have moderated to serious side effects, are only transiently effective in suppressing HBV, or are effective for only a small percentage of the general population of HBV-infected individuals. Even after universal implementation of neonatal vaccination there will still remain the existing carriers requiring on going treatment. There are no effective treatment for retrovirus associated disease, such as AIDS caused by HIV. Development of new effective drugs to eradicate HBV and retrovirus, such as HIV, in chronic carriers is, therefor of great potential importance.

SUMMARY OF THE INVENTION

The object of the invention is to provide a new class of drugs for treating hepatitis B and anti-retrovirus with high effective, low side action and no HBV rebound after stopping the administration of the drug.

Through widely and deep study, the inventors unexpectedly discover that dicaffeoylquinic acid derivatives and some noval caffeoylquinic acid derivatives can inhibit virus DNA replication and antigen expression of HBV and retrovirus with no rebound of HBV level after withdraw of drug. In addition, the dicaffeoylquinic acid derivatives and some new caffeoylquinic acid derivatives have potential effects on HIV. The completeness of this invention based on above discovery.

The first object of the invention relates to the new use of dicaffeoylquinic acid derivatives of formula I for treating Hepatitis B and diseases associated with retrovirus (such as HIV).

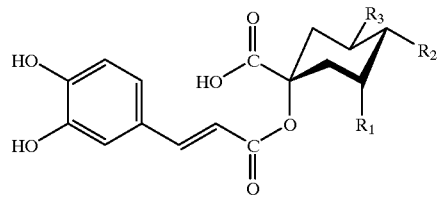

In which $R_1$, $R_2$ and $R_3$ may be the same or different and represent OH or caffeoyloxy group. When $R_1$ is caffeoyloxy group, both $R_2$ and $R_3$ represent OH; or When $R_2$ is caffeoyloxy group, both $R_1$ and $R_3$ represent OH; or When $R_3$ is caffeoyloxy group, both $R_1$ and $R_2$ represent OH.

The second object of the invention relates to the new dicaffeoylquinic acid derivatives of formula II.

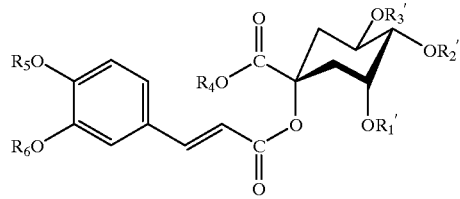

In which $R_1'$, $R_2'$ and $R_3'$ may be the same or different and represent H, $C_{1-6}$ alkyl group.

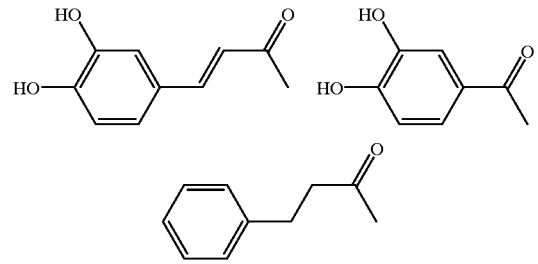

provided that $R_1'$, $R_2'$ and $R_3'$ can not be H at the same time, $R_1$ is $C_{1-6}$ alkyl group or M that is alkali metal such as Na, K et al, Both $R_2$ and $R_3$ represent H, $C_{1-6}$ alkyl group or $CH_3CO$.

The present invention also relates to the pharmaceutical composition containing the compound of formula I which have good inhibitory effects on HBV and retrovirus such as HIV.

According to the invention, the pharmaceutical composition may contain any kinds of pharmaceutically acceptable excipients, additives or carriers.

According to the invention, the compounds of formula I and II or the pharmaceutical composition containing the same in the present invention can be used to treat the diseases relate to HBV and retrovirus, especially the diseases caused by the infection with HBV or HIV.

According to the invention, the pharmaceutical composition of the present invention can be formulated in the forms of oral or parental preparations such as tablet, capsule, granula and injection.

According to the invention, the compounds of formula I or II may be prepared by synthesis or obtained from plants such as *Inula britannic*.

According to the invention, the preferred anti-HBV and retrovirus compound of the present invention is 1,5-di-O-caffeoylquinic acid as formula III.

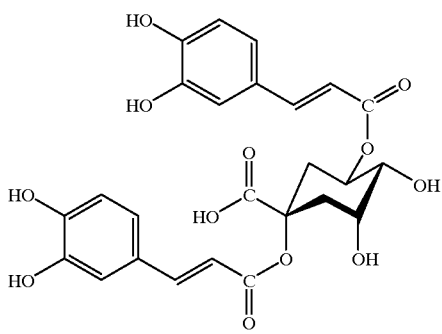

According to the invention, 1,5-di-O-caffeoylquinic acid can be isolated from *Inula britannic*. The isolated route is shown as below:

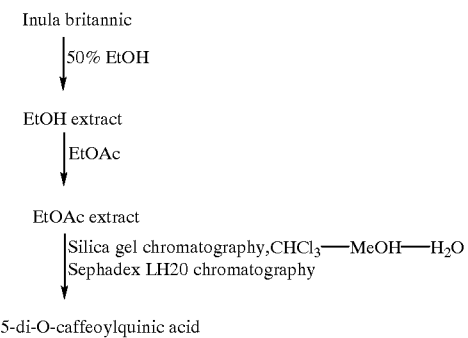

According to the invention, 1,5-di-O-caffeoylquinic acid is also synthesized as below:

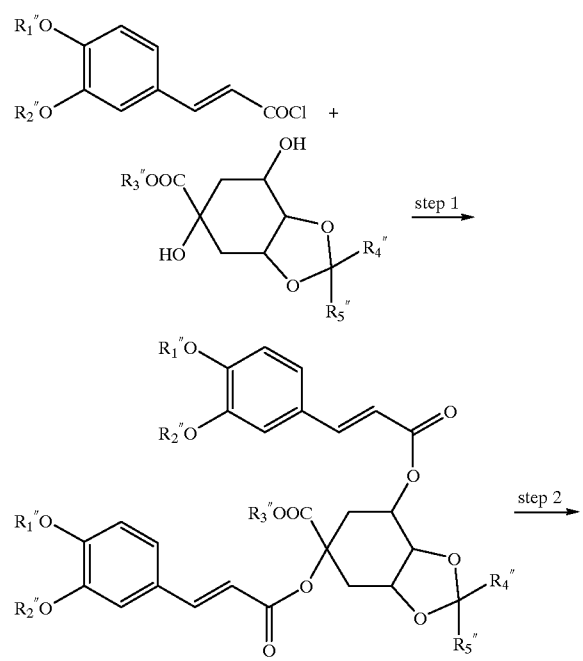

-continued

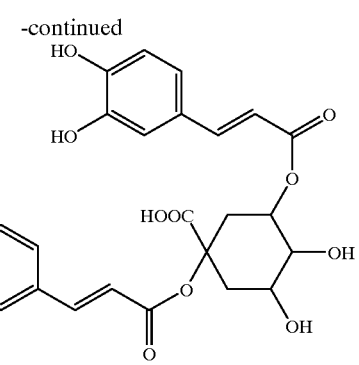

n which $R_1''$ and $R_2''$ may be the same or different and represent $C_nH_{2n-1}OCO$ in which n=1–6 or $R_1''$ and $R_2''$ together represent one carbonyl or —$CCl_2$—;

$R_3''$ is H, or M that is alkali metal such as Na, K et al or alkali earth metal such as Ca, Mg, Ba, et al. or $NH_4'$, $R_4'$ and $R_5'$ may be the same or different and represent H, $C_{1-6}$ alkyl or $C_{6-10}$ aryl or $R_4'$ and $R_5'$ together with adjacent carbon atom represent $C_{3-7}$ carbocycle such as $(CH_2)_5$.

Step 1 may be performed in route 1 or route 2:

Route 1: heated at the temperature range from 60° C. to 120° C. in vacuum and inorganic or organic bases such as $BaCO_3$, $K_2CO_3$, $Na_2CO_3$, $NaHCO_3$ may be added or not.

Route 2: solvents are added and may be any solvent provided that said solvent does not adversly affect to the reaction, such as, pyridine, triethylamine, dimethyl formamide, dimethyl sulfoxide, dichloromethane, trichloromethane, benzene, methylbenzene (toluene), acetone et al. Bases are added such as pyridine dimethylaminopyridine, triethylamine, $K_2CO_3$, $Na_2CO_3$ et al. temperature range from –4° C. to 100° C.

Step 2: Reaction mixture was hydrolyzed by acid such as dilute HCl or HOAc followed by the inorganic or organic base such as $NaHCO_3$, $Na_2CO_3$, $KHCO_3$, $K_2CO_3$.

DETAILED DESCRIPTION OF THE INVENTION

Figure 1:
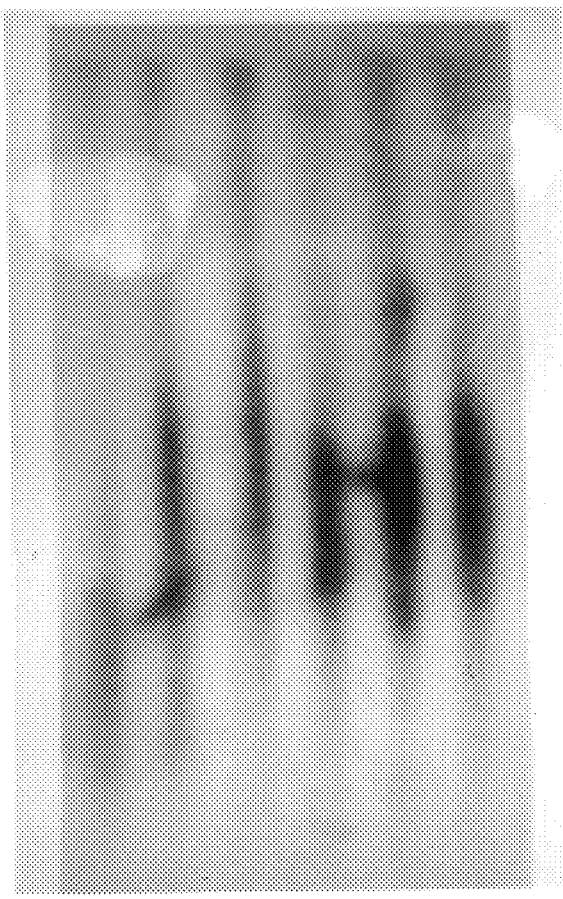
FIG. 1 is a photograph that shows that Southern blot analysis of extracellular DNA (culture medium) of untreated (right lane) and compound A treated (15.625, 31.25, 62.5, 125 and 250 ug/ml) 22.15 cells and molecular weight marked is show on the left.
Figure 2A:
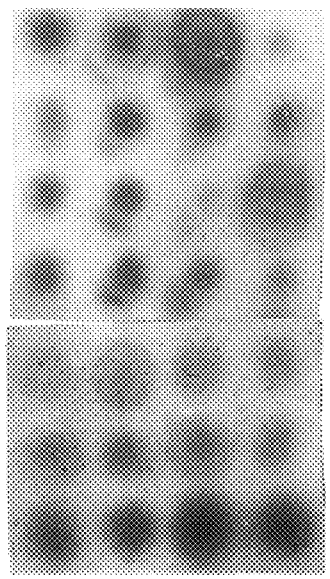
FIG. 2A is a photograph that shows that DHBV DNA dot blot hybridization of serum sample from seven ducks before (TO), during T7 and T14) and after treating with Normal Saline.
Figure 2B:
FIG. 2B is a photograph that shows that DHBV DNA dot blot hybridization of serum sample from seven ducks before (TO), during T7 and T14) and after treating with ACV at a dose of 50mg/Kg/day. ACV was administered by mouth twice daily for 14 days.
Figure 2C:
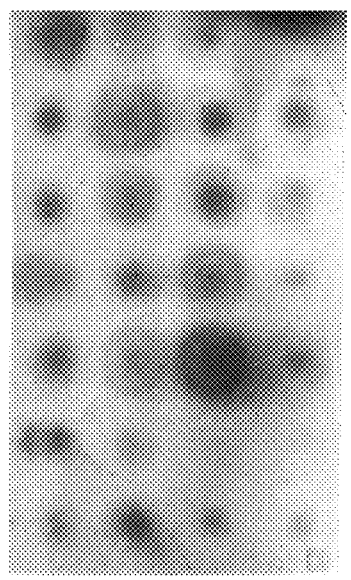
FIG. 2C is a photograph that shows that DHBV DNA dot blot hybridization of serum sample from seven ducks before (TO), during T7 and T14) and after treating with compound A at a dose of 5mg/Kg/day. Compound A was administered by mouth twice daily for 14 days.
Figure 2D:
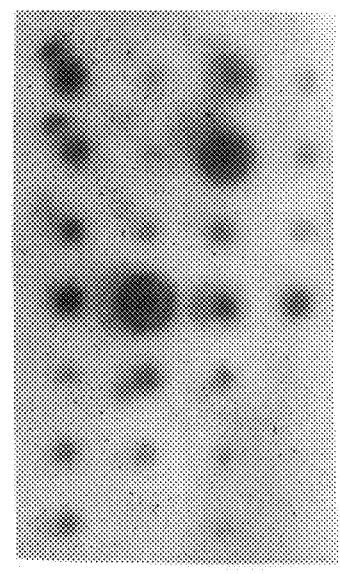
FIG. 2D is a photograph that shows that DHBV DNA dot blot hybridization of serum sample from seven ducks before (TO), during T7 and T14) and after treating with compound A at a dose of 12.5mg/Kg/day. Compound A was administered by mouth twice daily for 14 days.
Figure 2E:
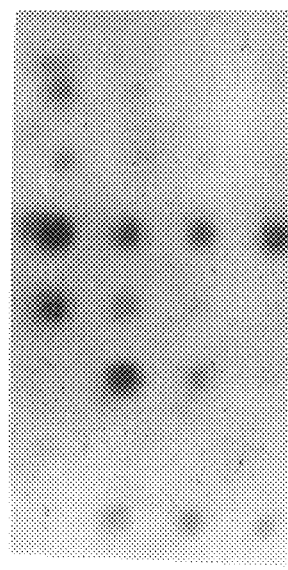
FIG. 2E is a photograph that shows that DHBV DNA dot blot hybridization of serum sample from seven ducks before (TO), during T7 and T14) and after treating with compound A at a dose 50mg/Kg/day. Compound A was administered by mouth twice daily for 14 days.
Figure 3A:
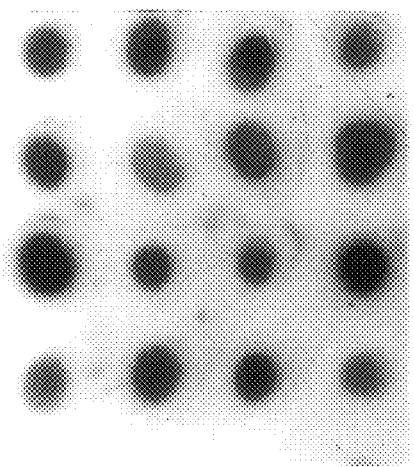
FIG. 3A is a photograph that shows that DHBV DNA dot blot hybridization of serum sample from seven ducks before (TO), during T5 and T10) and after (P3) treating with Normal Saline.
Figure 3B:
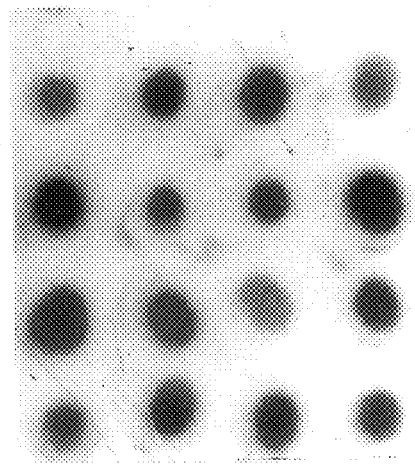
FIG. 3B is a photograph that shows that DHBV DNA dot blot hybridization of serum sample from seven ducks before (TO), during T5 and T10) and after treating ACV at a does of 50mg/Kg/day. ACV was administered by mouth twice daily for 14 days.
Figure 3C:
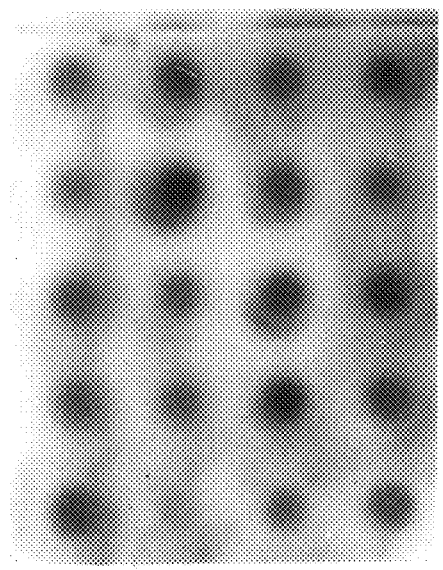
FIG. 3C is a photograph that shows that DHBV DNA dot blot hybridization of serum sample from seven ducks before (TO), during T5 and T10) and after treating with compound A at a dose of 12.5mg/Kg/day. Compound A was administered by mouth twice daily for 14 days.
Figure 3D:
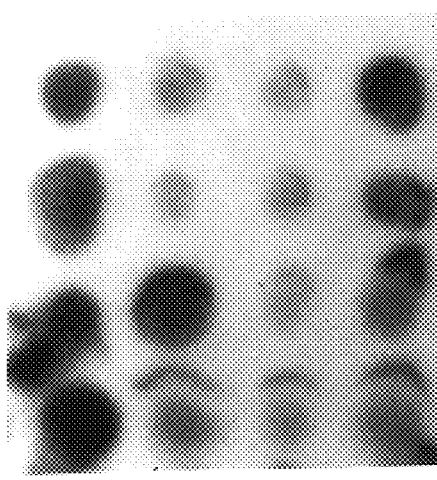
FIG. 3D is a photograph that shows that DHBV DNA dot blot hybridization of serum sample from seven ducks before (TO), during T5 and T10) and after treating with compound A at a dose of 50mg/Kg/day. Compound A was administered by mouth twice daily for 14 days.

The invention will be further described with the inhibitory effects of 1,5-di-O-caffeoylquinic acid (which will be abbreviated as compound A below) on HBV in vitro and in vivo and on HIV in vitro.

The inhibitory effects of compound A on HBV and HIV in vitro will be evaluated by the inhibitory test on HBV DNA ploymerase (HBV DNAp), synthesis and secretion of HBeAg and HBsAg, replication of HBV DNA in culture medium of HBV DNA transfected cell line (HepG2 derivative 2.2.15) and on HIV in $MT_4$ cells. The inhibitory effects of compound A on HBV in vivo will be evaluated on the model of duck infected with DHBV.

1. Materials and methods used in the anti-HBV test of compound A 1.1 Materials 1.1.1 Virus, cells and animals HBV particles purified by ultracentrifugation from the patients whose bloods were strong positive (+++) for HBsAg, HBeAg, HBV DNA was supplied Beijing Medical University. 2.2.15 cells derived from HBV DNA transfected Hep G2 cells were generously provided by Beijing Medical University.

DHBV: serum of Shanghai ducks with DHBV DNA positive(+++), store in −70° C.

Animal: <1 day old Peking (Beijing) ducks, from Nanyuan ducks farm, Beijing.

1.1.2 Reagents

HBV and DHBV DNA plasmid: supplied by Li Zhuang, Institute of Medicine and biotechnology, Chinese Academy of Medical Sciences.

$\alpha^{32}$P-dCTP: from Furei biotechnology engineering Co., Beijing, 3H-dTTP: DuPonds DMEM (Dulbecco's Modified Eagle Medium), Fetal calf serum, G-418 (Genenticin): from GIBICO BRL, U.S.A.

HBsAg and HBeAg protocol: supplied by Beifang Institute of Immune Reagent, Beijing.

1.2 Methods 1.2.1 HBV DNA polymerase assay

Assay was performed as described by Hantz (Antiviral Res 4(1984) 187–199) with minor modification. The Reaction mixture consisted of HBV DNA polymerase in viral particles in 200 mmol.l$^{-1}$ of Tris-HCl pH 7.6, 200 mmol.l$^{-1}$ of $NH_4Cl$. 50 mmol.l$^{-1}$ of $MgCl_2$, 10 mmol.l$^{-1}$ of 2-mercaptoethanol, 2% Nonidet P-40 and 300 $\mu$mol.l$^{-1}$ concentrations of deoxynucleotide triphosphates except for [$^3$H]dTTP, which was included in the assay at 20 $\mu$ci.ml$^{-1}$. Compound A at various concentrations was added. The mixtures were incubated at 37° C. for 4 h prior to spotting on Whatman No.3 filter paper which was washed 4 times with cold 5% trichloroacitic acid, then with ethanol. The HBV DNA polymerase activity as measure of the incorporation of the radionucleotide into the viral DNA was counted in a Recbeta (LKB)scintilation counter.

1.2.2 Determination of anti-HBV activity in 2.2.15 cells 1.2.2.1 Culture of 2.2.15 cells Hep G2 2.2.15 cell lines were maintained in DMEM supplemented with 10% fetal calf serum (FCS) and 100 units.ml$^{-1}$ of penicillin and streptomycin, 380 $\mu$g.ml$^{-1}$ of G418 in a humidified atmosphere containing 5% $CO_2$ at 37° C. The cultures were passenged by trypsinization every 4 days. For bioassays cells were plated in 24-well plates at a density of 1.0×10$^5$ cells/well. Two-day-old cultures were treated with various concentrations of drug in DMEM containing 10 FCS. The drug was left in the medium for 4 days, and then the medium was aspirated and the fresh medium containing the same concentration of drug was added. At the end of three 4-day periods, the cells were harvested. The aliquot of the culture medium was used for the estimation of the HBV surface antigen (HBsAg) and HBV e antigen (HBeAg).

1.2.2.2 Cytotoxicity test

Two-day-old cultures were treated with various concentrations of drug for 4 days, and then the medium was aspirated. The viability of cells was determined by MTT.

1.2.2.3 Determination of effects on drug on HBsAg and HBeAg

HBsAg and HBeAg in the culture medium were determined according to the protocol respectively. The culture medium (200 $\mu$l) was absorbed on beads containing antibody to HBsAg/HBeAg in the presence of the conjugate. After overnight incubation, the beads were washed 6 times with 0.01 mol.ml$^{-1}$ PBS containing 0.05% Tween-80 and incubated with 200 $\mu$l of [$^{125}$I] anti-HBs(Hbe) overnight. The beads were washed 6 times as above. The amounts HBsAg/HBeAg as measure of cpm of [$^{125}$I] labeled immunocomplex was counted on $\gamma$-counter.

1.2.2.4 The inhibitory test on HIV DNA replication in 2.2.15 cells

DNA extraction in 2.2.15 cells: Total DNA was isolated from 2.2.15 cells, cells was washed in PBS and lysed in a solution containing 50 mmol.l$^{-1}$ Tris-HCl (pH 7.5). 10 mmol.l$^{-1}$ EDTA. 1% SDS and 50 $\mu$g.ml$^{-1}$ of proteinase K (Sigma). After incubation at 37° C. for 4 h, total DNA was extracted in phenol-chloroform-isoamyl alcohol (25:24:1) followed by two extractions with chloroform-isoamyl alcohol. The DNA was precipitated with ¹/₁₀ vol NaOAc and 2.5 vol ethanol overnight at −70° C. After centrifugation at 12000 g for 10' at room temperature, the pellet was rinsed two times with cold 75% ethanol, dried and resuspended in Tris/EDTA buffer, then stored at −20° C.

Southern blotting: Samples of DNA were electrophoresed on a 1% agarose gel and transferred to nitrocellulose. Hybridization was done overnight at 42° C. with a full length HBV genomic DNA probe radiolabeled by [$^{32}$P]-nick translation. HBV DNA species were visualized by autoradiography. Relative levels of densities on the exposed X-ray film representing the episomal HBV DNA were compared by densitometry.

1.2.3 The ant-DHBV test in ducks

One-day-old ducklings were infected with a 200 μl intravenous injection of DHBV-positive serum containing $10^{11}$ viral genome equivalents per milliliter. Treatment began when ducklings were 7 days old. A total 89 seven-day-old viraemic ducks were distributed at random into five groups. Three groups were administered for 14 days with compound A at the dosage of 5, 12.5, and 50 mg.kg of body weight$^{-1}$.day$^{-1}$, given orally in two equal (morning and evening) dose dissolved in normal saline (NS). Other two groups were treated with NS and Acyelorvir (ACV) at the dosage of 50 mg.kg of body weight$^{-1}$.day$^{-1}$ instead of compound A respectively. Post-treatment follow-up was carried over a period of 5 days. Blood samples were obtained repectively from the leg vein of all ducks and stored at −70° C. after serum separation, prior to treatment, weekly during the treatment, and for 5 days after cessation of treatment. They were screened for presence of DHBV DNA by dot blot hybridization.

Detection of DHBV DNA by dot blot hybridization

DHBV DNA in serum was analyzed by molecular hybridization using full length DHBV DNA clones in PB325. The DHBV DNA insert was purified by agarose gel electrophoresis after digestion with EcoRI. The DHBV DNA was radiolabeled with $\alpha^{32}$P-dCTP random oligopriming with Klenow fragment. Dot blot hybridization was carried out by the method of Scotto et al. Briefly, an aliquot (200 μl) serum was spotted onto a nylon membrane (Hybond-N, Amersham International, England) in dot blot manifold and denatured with 0.5 M NaOH—NaCl at room temperature for 30 min. Each spotted sample was neutralized in 1M Tris.HCl-1.5M NaCl (pH8.0). The DNA on the membrane was fixed by heating at 80° C. for 2 h, and prehybridization at 37° C. overnight in 50% formamide, 5×Denhardt's, 6×SSC, 10 M EDTA, 0.5% SDS and 10 mg/ml of calf thymus DNA. Hybridization was initiated by adding DHBV [$^{32}$P] DNA probes at $10^6$ cpm/ml at the same prehybridization conditions overnight. The membrane was washed in 3×SSC-0.1% SDS at room temperature, 42° C. and 65° C. for 10 min respectively. After hybridization the membranes were air-dried and exposed for periods of up to 14 days at −70° C. with Kodak film with an enhancer screen. The amount of viral DNA were assayed by both densitometry and image analysis of autoradiographic membranes.

2. RESULTS 2.1 The inhibition of compound A on the HBV DNA polymerase

The inhibition of the HBV DNA polymerase by compound A and PFA as positive-control are shown in table 1.

TABLE 1

The inhibition of the HBV DNA polymerase by compound A and PFA

| Drug | Compound A | | PFA | |
|---|---|---|---|---|
| concentration (μg/ml) | cpm | Inhibitory rate (%) | cpm | Inhibitory rate (%) |
| 0 | 11093 ± 99 | | 11093 ± 99 | |
| 1 | 9856 ± 201 | 11.2 ± 1.9 | 10267 ± 77 | −5.2 ± 15.3 |
| 10 | 7990 ± 79 | 30.3 ± 0.8 | 5495 ± 218 | 44.4 ± 2.3 |
| 100 | 3522 ± 51 | 68.4 ± 0.5 | 3065 ± 67 | 69.7 ± 0.7 |
| 1000 | 1983 ± 159 | 82.3 ± 1.5 | 2377 ± 329 | 76.8 ± 3.4 |

PFA showed dose-dependent inhibitory effect on HBV DNAp. Its 50% inhibition concentration (IC$_{50}$) as 23.2 μg · ml$^{-1}$ was identical to the reported.

Compound A had a significant dose-dependent inhibitory effect on HBV DNA DNAp. Its 50% inhibition concentration (IC$_{50}$) was 30.6 μg.ml$^{-1}$.

2.2 The anti-HBV effects of compound A in 2.2.15 cells 2.2.1 Cell growth of 2.2.15 cells Compound A did not show toxicity to the Hep G2 cell lines and 2.2.15 cells at the concentration of 1.0 μg.ml$^{-1}$.

2.2.2 Effects of compound A on the production of HBsAg and HBeAg 2.2.15 cells were plated into 24-wells plate and allowed to attach two days, then various concentrations of compound A were added for 4, 8 and 12 days. When the HBsAg and HBeAg in the culture medium were examined, marked suppression of HBsAg and HBeAg was observed in a dose-dependent manner.

Measurement of the levels of HBsAg and HBeAg from the culture medium with the various concentrations of the compound A revealed that compound A had significant dose-dependent inhibitory effect on HBsAg and HBeAg. The IC$_{50}$ of compound A for inhibition of production of HBeAg and HBsAg were about 21~78 μg.ml$^{-1}$ and 21~165 μg.ml$^{-1}$, respectively.

TABLE 2

Effects of compound A on the production of HBsAg and HBeAg

| drug conc. (μg/ml) | culture Time (day) | HBeAg cpm | Inhibit rate (%) | HBsAg cpm | Inhibit rate (%) |
|---|---|---|---|---|---|
| 0 | 4 | 5205.2 ± 136.2 | | 1211.6 ± 39.1 | |
|  | 8 | 8231.8 ± 172.9 | | 1163.2 ± 41.8 | |
|  | 12 | 8499.4 ± 167.7 | | 759.0 ± 15.6 | |
| 7.81 | 4 | 4764.0 ± 212.0 | 8.94 ± 4.29 | 1032.6 ± 10.8** | 17.21 ± 1.03 |
|  | 8 | 7400.7 ± 163.3* | 10.43 ± 2.05 | 979.3 ± 42.3* | 18.54 ± 4.26 |
|  | 12 | 7188.3 ± 197.5** | 15.93 ± 2.40 | 617.0 ± 27.2** | 24.17 ± 4.63 |
| 15.63 | 4 | 4264.0 ± 192.1* | 19.06 ± 3.89 | 941.1 ± 27.2** | 26.00 ± 2.62 |
|  | 8 | 5707.0 ± 567.8** | 31.70 ± 7.1 | 888.9 ± 16.3** | 27.65 ± 1.64 |
|  | 12 | 6211.5 ± 183.3** | 27.80 ± 2.23 | 574.6 ± 18.8** | 31.37 ± 3.20 |
| 31.25 | 4 | 3503.4 ± 328.9** | 34.47 ± 6.66 | 824.2 ± 29.7** | 37.24 ± 2.86 |
|  | 8 | 4906.8 ± 196.4** | 41.75 ± 2.47 | 808.5 ± 18.9** | 35.75 ± 1.90 |
|  | 12 | 5991.2 ± 291.9** | 30.47 ± 3.55 | 546.5 ± 8.7** | 36.15 ± 1.48 |
| 62.5 | 4 | 3181.4 ± 181.7** | 40.99 ± 3.68 | 717.5 ± 12.2** | 47.48 ± 1.17 |
|  | 8 | 4631.7 ± 196.8** | 45.21 ± 2.47 | 699.7 ± 20.2** | 46.72 ± 2.03 |
|  | 12 | 4603.5 ± 66.76** | 47.33 ± 0.81 | 464.2 ± 7.50** | 50.14 ± 1.28 |

TABLE 2-continued

Effects of compound A on the production of HBsAg and HBeAg

| drug conc. (µg/ml) | culture Time (day) | HBeAg cpm | Inhibit rate (%) | HBsAg cpm | Inhibit rate (%) |
|---|---|---|---|---|---|
| 125 | 4 | 2867.7 ± 53.8** | 47.35 ± 1.09 | 618.5 ± 25.4** | 57.00 ± 2.44 |
|  | 8 | 4052.1 ± 150.6** | 52.49 ± 1.89 | 617.7 ± 20.6** | 54.99 ± 2.08 |
|  | 12 | 4014.8 ± 82.8** | 54.48 ± 1.01 | 416.1 ± 14.7** | 58.32 ± 2.51 |
| 250 | 4 | 2034.2 ± 100.3** | 64.23 ± 2.03 | 563.5 ± 23.1** | 62.29 ± 2.22 |
|  | 8 | 3081.5 ± 181.7** | 64.67 ± 2.28 | 480.8 ± 46.5** | 68.79 ± 4.68 |
|  | 12 | 3025.4 ± 74.0** | 66.50 ± 0.90 | 367.5 ± 6.70** | 66.60 ± 1.15 |
| ACV | 4 | 3910.9 ± 57.6** | 26.22 ± 1.17 | 710.1 ± 65.7** | 48.20 ± 6.31 |
|  | 8 | 6101.9 ± 96.17** | 26.75 ± 1.21 | 870.1 ± 51.1** | 29.54 ± 5.15 |
|  | 12 | 8194.1 ± 111.5 | 3.71 ± 1.36 | 622.5 ± 58.8 | 23.22 ± 2.01 |

*and **: drug group Vn placebo p < 0.05 and 0.01

2.2.3 Inhibition of HBV DNA replication by compound A

Compound A may inhibit HBV DNA replication in a dose dependent manner as shown in FIG. 1.

The FIG. 1 shows the inhibitory effect of compound A at various concentration on HBV DNA replication.

2.3 The inhibitor effects of compound A on DHBV in ducks

All ducks remained healthy and mean weight of both placebo and treated groups increased comparably during the study. Viremia was monitored by serum dot-blot hybridization. Ducks in the negative control group keep negative for viral DNA throughout the entire period of study. Persistent infection of ducks is evident. This maintained unchanged in the placebo-treated group. Treatment with ACV, effective anti-HBV anti-HBV drug as reported, resulted in a substantial decrease of DHBV DNA from the sera during the 14 days of therapy in all 7 treated birds. At day 5 after cessation of treatment, the viraemia returned to a level higher than that of pretreatment by 43%. In the groups of compound A treated animals, the viraemia from the serum were decreased in dose- and time-dependently manner. A potent inhibition of viraemia (87%) was observed at day 14 from treatment in the group treated with compound A at a dosage of 50 mg.kg of body weight$^{-1}$.day$^{-1}$, and the viraemia remained at the lower level 4 days after the withdrawn of compound A, which was significantly lower than those after NS and ACV. Preliminary results showed that the maximal tolerance dose in duck was higher than 4 g.kg$^{-1}$.

Compound A has dose- and time-dependent inhibitory effect on DHBV DNA in ducks. Compound A has strange inhibition of DHBV DNA at a dosage of 50 mg.kg of body weight$^{-1}$.day$^{-1}$, and the DHBV DNA remained at the lower level 5 days after the withdrawn of compound A, which was significantly lower than those after NS and ACV. Preliminary results showed that the maximal tolerance dose in duck was higher than 4 g.kg$^{-1}$.

4. The anti-HIV effects of compound A 4.1 Materials and Methods 4.1.1 Cells and virus A human T-cell leukemia cell line. MT4 cells, was used in this study. It was maintained in RPMI-1640 medium supplemented with 10% FCS. 100 U/ml of penicillin, and 100 µg/ml of streptomycin at 37° C. in a humidified atmosphere of 5% $CO_2$. Cell cultures were split into fresh medium every 4 days.

HIV-1 virus was propagated in MT4 cells. The cell-free supernatants of HIV-1 infected MT4 cell culture were used as virus stocks and frozen at −80° C. until used. The 50% tissue culture infected dose ($TCID_{50}$) of the cell-free virus stock was determined by end-point titration with MT4 cells in 96-well microdilution plates.

4.1.2 Assay of Cytotoxicity

The cytotoxicity of compound A in uninfected MT4 cells was evaluated by the 3,-(4,5-dimethylthiazol-2-yl)-2,5-diphenyltetrazolium bromide (MTT) method. MT4cells (0.1

TABLE 3

The inhibitor effects of compound A on DHBV DNA in ducks
(K Grayness of the dot. X ± SD, n = 7)

| Treatment time | placebo | acyclovir 50 mg/kg | Compound A 5 mg/kg | Compound A 12.5 mg/kg | Compound A 50 mg/kg |
|---|---|---|---|---|---|
| day 0 | 4.9 ± 2.1 | 6.3 ± 4.2 | 3.4 ± 1.2 | 2.6 ± 1.9 | 4.0 ± 2.5 |
| day 7 | 5.3 ± 2.7 | 0.1 ± 0.3** | 2.7 ± 0.9 | 1.3 ± 1.3 | 1.3 ± 1.1* |
| day 14 | 4.4 ± 2.3 | 0.0 ± 0** | 1.3 ± 1.3** | 0.6 ± 1.1* | 0.5 ± 1.4** |
| P5 | 4.0 ± 2.5 | 9.0 ± 8.6 | 2.5 ± 1.5 | 1.9 ± 1.4 | 0.5 ± 0.7** |

*and **: Vs with day 0, P < 0.05 ✗‖P < 0.01. p5: day 5 after the withdraw of drug.

3. Conclusion

Compound A has anti-HBV effects in vitro and in vivo.

Compound A inhibits HBV DNA polymerase, the production of HBsAg and HBeAg in 2.2.15 cells in a dose-dependent manner with $IC_{50}$ as 14.3–30.6 µg/ml, 21–78 µg/ml and 21–165 µg/ml respectively. Compound A has no obvious harmful effects on 2.2.15 cells at 500 µg/ml.

ml) suspended in culture medium at 1×10$^5$ cells/ml were seeded into wells of 96-well microplates containing various amounts of compound A. After incubation at 37° C. for 4 days, 10 µl of MTT solution (7.5 mg/ml) was added to culture to stain viable cells. After 4 h, 100 µl of solvent (10% Triton X-100 and 0.4% HCl isopropanol)was added to cultures to solubilizes formazan. After an overnight incubation, the absorbency of each well was measured using a microplate reader (Bio-Rad, model 450) at 560 nm.

4.1.3 Anti-HIV-1 assay

MT4 cells in culture were counted by trypan blue exclusion method. The MT4 cells suspended in a small volume of RPMI-1640 medium without FCS and infected with HIV-1 at 200 TCID$_{50}$ viruses per $10^6$ cells. The mixture of MT4 cells and virus was subsequently incubated at 37° C. in a humidified atmosphere of 5% CO2 for 1 hr to allow virus to adsorbed to cells. Unabsorbed viruses were then removed by washing one with 10 of the fresh medium and centrifuged at 1000 rpm for ten minutes. The cells were suspended in the medium and distributed into 12-well microculture plates ($10^6$ cells/3 ml/well). Various concentrations of compound A were added to the cell culture immediately. After 4-day incubation at 37° C. in a humidified atmosphere containing 5% $CO_2$ the medium was aspirated and the fresh medium containing the same concentration of drug was added.

4.1.4 Observation of syncytia of infected MT4 cells

After 4-day incubation the syncytia of infected MT4 cells may be observed. After 7-day incubation the viable cells was evaluated by MTT method as described above.

4.1.5 Reverse transcriptase (RT) assay

The presence of HIV-1 RT in the supernatants of infected, drug-treated and infected, no drug treated MT4 cell culture was assayed. Cell culture fluids was clarified at 1000 rpm for 10 minutes to remove cellular debris. The supernatant samples (20 μl) in duplicate transferred to 5 ml plastic Falcon tubes, 10 μl of virus solubilization buffer [0.5% Triton X-100 in 0.8 M NaCl, 0.5 mM phenylmethysulfonyfluoride, 20% (v/v) glycerol and 50 mM Tris-HCl, pH 7.8] were then added to solubilize the viral particles in the supernatant samples and to release RT located in the viral core. 170 μl of reaction mixture (cocktail I) [52 mM Tris-HCl (pH 7.8), 10 mM $MgCl_2$, 2 mM dithiothreitol, 5 μg of poly(rA)-oligo(dT) per ml. 83 μg of dATP per ml, and 3 μCi of [$^3$H]TTP per ml] was then added and incubated at 37° C. for 2 hr. The incorporation of [$^3$H]TTP into DNA with poly(rA)-olgio(dT) template primer by viral RT was assessed by trichloroacetic (TCA) precipitation and filtered over a 27 nm diameter glass fiber filter. Tree millimeters of cold 10% TCA was added to precipitate DNA. The precipitate DNA was then collected on the filters in a Millipore sampling manifold, and was washed with additional 5 volumes of 5% TCA and 2 volumes of 70% ethanol. Radioactivity of the DNA on the filters was determined by a scintillation counter.

4.1.6 Therapeutic effects in mice infected with LP-BM5 murine retrovirus mice. Five-wk-old female C57BL/6 mice were used throughout the experiments. All mice were housed in sterile cages in a room supplied with filtrated air. They were given pelleted food and chlorinated water ad libitum.

Infection with LP-BM5 MuLV. Cell-free supernatants of LP-BM5 MULV were prepared by cocultivating G6 SC-1 clones with normal SC-1 cells for 5 days. Mice were inoculated intraperitoneally with 150 μl of stock solution containing $10^{3.4}$×C plaque-forming units and $10^{2.3}$ Mink-cell focks-forming units per millimeter.

Compound A was administered by oral route at one time a week, starting the next day after inoculation of viruses for 50 days. Then, the spleens were collected. Cell suspensions were prepared by repeated passage of whole spleen through a pipette, the capsule and debris were allowed to settle, and the supernatants containing cells were collected and washed twice in PBS. After erythrocytes were removed with FACS lysing solution, the spleen cells were suspended in the medium and distributed into 96-well microculture plates ($5 \times 10^3$ cells/100 μl/well), and Con A (2 μg/100 μl/well) and LPS (4 μg/100 μl/well) were added respectively in the meanwhile. Various concentrations of compound A were added to the cell culture immediately. After 56 hr incubation at 37° C. in a humidified atmosphere containing 5% $CO_2$ 3H-TdR was added (0.5 μCi/well). Incubation continued for 16 hr, then cells were collected on filter that was determined by a scintillation counter.

4.2 Results

The cytotoxicity of Compound A was determined by the MTT method. Even at a concentration of 1000 μg.ml$^{-1}$ compound A was markedly cytotoxic to MT4 cells.

After 4 days incubation, no syncytia were observed in the plates which was treated with compound A at the dosage over 25 μg/ml, in the meantime, syncytia were obvious in the untreated plates as shown in table 4.

TABLE 4

Inhibitory effects of compound A on HIV in MT4 cells (syncytia)

| Dose(μg/ml) | 1000TCID$_{50}$ | 100TCID$_{50}$ |
| --- | --- | --- |
| 50 | – | – |
| 25 | – | – |
| 12.5 | + | – |
| 6.25 | ++ | ++ |
| 3.13 | ++++ | +++ |
| 0 | ++++ | ++++ |

In the absence of compound A, about 72% of cells were killed by HIV after 7-days incubation. Compound A increased the amounts of viable cells dose-dependently as shown in table 5.

TABLE 5

Compound A increased the amounts of viable cells

| Dose | 1000 TCID$_{50}$ | | 1000 TCID$_{50}$ | |
| --- | --- | --- | --- | --- |
| (μg/ml) | O.D. | Inhibit rate (%) | O.D. | Inhibit rate (%) |
| 100 | 0.72 ± 0.10 | 61.5 | 0.78 ± 0.10 | 57.7 |
| 50 | 0.82 ± 0.05 | 74.8 | 0.80 ± 0.02 | 60.6 |
| 25 | 0.78 ± 0.03 | 69.9 | 0.83 ± 0.02 | 63.7 |
| 12.5 | 0.67 ± 0.05 | 55.0 | 0.77 ± 0.06 | 56.5 |
| 6.25 | 0.57 ± 0.06 | 40.0 | 0.68 ± 0.03 | 44.3 |
| 3.12 | 0.43 ± 0.03 | 21.1 | 0.49 ± 0.06 | 19.0 |
| 1.56 | 0.33 ± 0.04 | 7.2 | 0.41 ± 0.04 | 8.1 |
| 0 | 0.28 ± 0.01 | | 0.35 ± 0.02 | |

As shown in table 6. Compound A inhibit RT in MT4 cells infected with HIV, and its IC$_{50}$ was 17.1 μg/ml.

TABLE 6

Compound A inhibit RT in MT4 cells infected with HIV

| Drug concentration | Compound A | |
| --- | --- | --- |
| (μg/ml) | cpm | Inhibitory rate(%) |
| 0 | 7842 ± 115 | |
| 1 | 6051 ± 91 | 22.8 ± 1.9 |
| 10 | 4283 ± 89 | 45.4 ± 0.8 |
| 100 | 2456 ± 54 | 68.7 ± 0.5 |
| 1000 | 1528 ± 89 | 80.5 ± 1.5 |

As shown in table7, the immune system of mice infected with MuLV was significantly depressed. Compound A enhance the proliferation of lymphocyte induced by Con A in a degree near to that of AZT.

TABLE 7 compound A enhance the proliferation of lymphocyte induced by Con A

| Group | Con A (2.5 μg/ml) | | Con A (5 μg/ml) | |
|---|---|---|---|---|
| | cpm | RPI | cpm | RPI |
| Normal | 35631 ± 3018 | 100 | 56032 ± 4013 | 100 |
| NS | 13489 ± 1634 | 37.86 | 17921 ± 1771 | 31.98 |
| AZT (50 mg/kg) | 33212 ± 2609 | 93.21 | 53287 ± 2043 | 95.10 |
| Compound A (25 mg/kg) | 28627 ± 3206 | 80.34 | 49308 ± 2967 | 88.00 |
| Compound A (50 mg/kg) | 31579 ± 3312 | 88.63 | 51098 ± 3270 | 91.19 |

4.3 Conclusion

Compound A has potential inhibitory effects on HIV in vitro and in vivo. It restrain the appearance of syncytia, increase the amounts of viable cells, and inhibit RT in MT4 cells infected with HIV, and its $IC_{50}$ was 17.1 μg/ml. Compound A enhance the proliferation of lymphocyte of mice infected with MuLV.

5. Synthesis of compound A

Example 1

Synthesis of Compound A 44.9 mg of carbonylcaffeic acid chloride is thoroughly mixed with dry, powdered 25.4 mg of sodium acetone quinate in a flask immersed in an oil bath. The flask is put under vacuum and is heated first to 100° C. and then, slowly, to 140° C., maintaining this temperature for about 20–30 min. The molten mass is left to cool under vacuum, and then hydrolyzed with 20 ml of 80% HOAc on boiling water bath for 30 min. After HOAc is removed, and the residue (about 80 mg) is purified by silica gel chromatography, eluted with $CHCl_3$—MeOH—$H_2O$ (90:35:6). The title compound (about 45 mg) is obtained FEB-MS: m/z 609, 517, 499, 355, 337, 193, 163, EI-MS: m/z 354, 336, 180, 163. $^1$H-NMR: δ 19.6 (dd), 236 (dd), 2.48 (dd), 2.50 (dd), 3.75 (ddd), 4.24 (ddd), 5.37 (ddd), 6.20 (d), 6.25 (d), 6.80 (d), 6.81 (d), 6.96 (dd), 6.97 (dd), 7.11 (d), 7.13 (d), 7.50 (d), 7.53 (d), $^{13}$C-NMR: δ 35.4, 37.3, 69.4, 71.3, 72.9, 80.6, 115.4, 115.9, 116.3, 116.7, 123.1, 127.8, 146.6, 146.7, 146.8, 149.3, 166.9, 167.6.

Example 2

Synthesis of Compound A

A mixture of 44.9 mg of carbonylcaffeic acid chloride and 25.4 mg of sodium acetone quinate is treated with 10 ml of DMF and 10 mg of DMAP at room temperature overnight, and then 40 ml of water and EtOAc were added while stirring. The EtOAc solution is evaporated, and the residue is hydrolyzed with 20 ml of 80% HOAc on boiling water bath for 30 min. After HOAc is removed, the residue (about 85 mg) is purified by silica gel chromatography, eluted with $CHCl_3$—MeOH—$H_2O$ (90:35:6). The title compound (about 49 mg) is obtained. Its spectra data is the same as in example 1.

Example 3

Synthesis of Compound A 53.5 mg of dichloromethylenecaffeic acid chloride is thoroughly mixed dry, powdered 25.4 mg of sodium acetone quinate in a flask immersed in an oil bath. The flask is put under vacuum and is heated first to 100° C. and then, slowly, to 140° C. maintaining this temperature for about 20–30 min. The molten mass is left to cool under vacuum, and then hydrolyzed with 20 ml of 80% HOAc on boiling water bath for 30 min. After HOAc is removed, and the residue (about 80 mg) is purified by silica gel chromatography, eluted with $CHCl_3$—MeOH—$H_2$O (90:35:6). The title compound (about 45 mg) is obtained. Its spectra data is the same as in example 1.

Example 4

Synthesis of Compound A

A mixture of 53.5 mg of dichloromethylenecaffeic acid chloride and 25.4 mg of sodium acetone quinate is treated with 10 ml of DMF and 10 mg of DMAP at room temperature overnight, and then 40 ml of water and EtOAc were added while stirring. The EtOAc solution is evaporated, and the residue is hydrolyzed with 20 ml of 80% HOAc on boiling water bath for 30 min. After HOAc is removed, the residue (about 85 mg) is purified by silica gel chromatography, eluted with $CHCl_3$—MeOH—$H_2O$ (90:35:6). The title compound (about 45 mg) is obtained. Its spectra data is the same as in example 1.

We claim:

1. A method for the treatment of Hepatitis B and disease associated with retrovirus by administering to a patient in need thereof, a dicaffeoylquinic acid derivative of the formula:

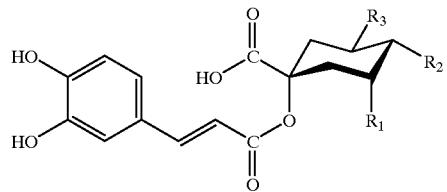

in which $R_1$, $R_2$ and $R_3$ may be the same or different and represent OH or caffeoyloxy group, when $R_1$ is caffeoyloxy group, both $R_2$ and $R_3$ represent OH; or when $R_2$ is caffeoylxy group, both $R_1$ and $R_3$ represent Oh; when $R_3$ is caffeoyloxy group, both $R_1$ and $R_2$ represent OH.

2. The method according to claim 1, wherein said retrovirus in HIV.

3. The method according to claim 1 wherein said dicaffeoylquinic acid is 1,5-di-O-caffeoylquinic acid having the following formula:

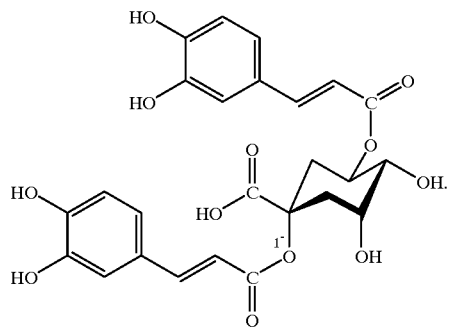

4. The method according to claim 3 wherein the retrovirus is HIV.

5. Dicaffeoylquinic derivatives of the following formula II:

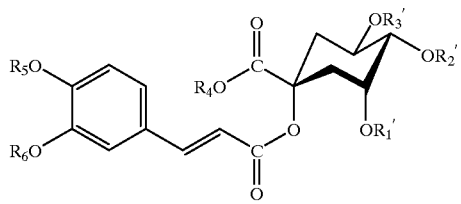

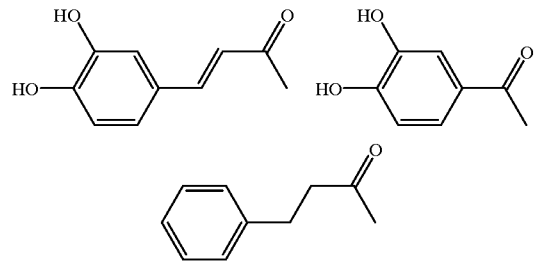

in which which $R_1'$, $R_2'$ and $R_3'$ may be the same or different and represent H, $C_{1-6}$ alkyl group, provided that $R_1'$ and $R_2'$ and $R_3'$ can not be H at the same time, $R_4$ is $C_{1-4}$ alkyl group or M is alkali metal, wherein both $R_5$ and $R_6$ represent H, $C_{1-4}$ alkyl grpup or $CH_3CO$.

6. A pharmaceutical composition for the treatment of Hepatitis B and diseases associated with retrovirus comprising dicaffeoylquinic acid derivatives of formula II as follows:

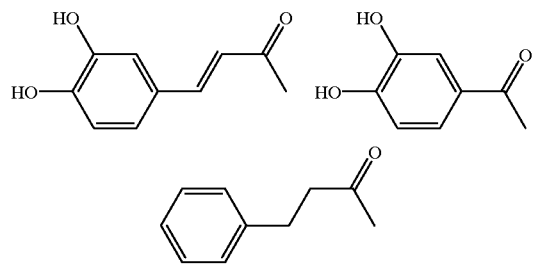

in which $R_1'$ and $R_2'$ and $R_3'$ may be the same or different and represent H, $C_{1-6}$ alkyl group, provided that $R_1'$ and $R_2'$ and $R_3'$ can not be H at the same time, $R_4$ is $C_{1-4}$ alkyl group or is alkali metal, wherein both $R_5$ and $R_6$ represent H, $C_{1-4}$ alkyl group or $CH_3CO$.

* * * * *